United States Patent
Kazatchkov et al.

(10) Patent No.: US 6,247,892 B1
(45) Date of Patent: Jun. 19, 2001

(54) CONTINUOUS FLOW ROTARY PUMP

(75) Inventors: Lev Kazatchkov; Lucas Varela, both of Mendoza (AR)

(73) Assignee: IMPSA International Inc., Pittsburgh, PA (US)

( * ) Notice: Subject to any disclaimer, the term of this patent is extended or adjusted under 35 U.S.C. 154(b) by 0 days.

(21) Appl. No.: 09/361,108

(22) Filed: Jul. 26, 1999

(51) Int. Cl.[7] .................................................. F01D 1/24
(52) U.S. Cl. ............................................. 415/68; 415/900
(58) Field of Search ............................... 415/66, 68, 71, 415/72, 900; 416/DIG. 2

(56) References Cited

U.S. PATENT DOCUMENTS

| | | |
|---|---|---|
| 1,071,042 | 8/1913 | Fuller . |
| 2,470,794 | 5/1949 | Snyder . |
| 3,083,893 | 4/1963 | Dean .................................. 415/68 X |
| 3,276,382 | 10/1966 | Richter . |
| 4,779,614 | 10/1988 | Moise . |
| 4,846,152 | 7/1989 | Wampler et al. . |
| 4,908,012 | 3/1990 | Moise et al. ....................... 415/900 X |
| 5,040,944 | 8/1991 | Cook ...................................... 415/72 |
| 5,112,292 | 5/1992 | Hwang . |
| 5,209,650 | 5/1993 | Lemieux . |
| 5,507,629 | * 4/1996 | Jarvik ............................... 415/900 X |
| 5,588,812 | 12/1996 | Taylor et al. ..................... 415/900 X |
| 5,678,306 | 10/1997 | Bozeman, Jr. et al. ......... 415/900 X |
| 5,692,882 | 12/1997 | Bozeman, Jr. et al. ......... 415/900 X |
| 5,707,218 | 1/1998 | Maher et al. .................... 415/900 X |
| 5,851,174 | * 12/1998 | Jarvik ............................... 415/900 X |

* cited by examiner

Primary Examiner—John E. Ryznic
(74) Attorney, Agent, or Firm—Fulbright & Jaworski

(57) ABSTRACT

A continuous flow axial-flow pump for impelling a fluid under a continuous pattern without kinetic side effects to minimize and eliminate damage to fluid, the pump comprising two axial adjacent rotors rotating in opposite directions.

3 Claims, 5 Drawing Sheets

CONTINUOUS FLOW ROTARY PUMP

BACKGROUND OF THE INVENTION

1. Field of the Invention

The present invention relates to a continuous flow rotary pump, preferably a continues axial flow rotary pump for impelling liquid through at least one stage, by transferring energy from rotating elements of the pump to a continuous fluid stream, and more preferably the invention relates to a continuous axial flow rotary pump for use in blood circulation assistance, either in intravascular or extravascular circuits, with maximized efficiency and with no, or at least extremely minimized, blood damage, blood clotting, as well as minimum pump dimensions.

Although particular reference will be made in the present specification to a blood pump, it should be understood that the present pump is for use in any other field wherein any fluid must be transferred from one place to another one, either in a closed circulation loop or in any open circuit or path.

2. Description of the Prior Art

It is well known to provide an axial-flow rotary pump comprising a generically cylindrical casing and/or stator with a rotor, or a plurality of rotors mounted inside the stator to drive a fluid through the pump. The driving of the liquid to transfer the same from an inlet of the pump to a pump outlet is based in the provision of energy to the liquid to increase the fluid pressure thereof. This energy, however, provides several undesired side effects. The elimination of these effects without impairing the pumping efficiency of the pump has been the aim of many developments in the field of pumps, particularly when handling of sensitive fluids, such as explosives, blood, etc., is involved.

Contours, sizes, assemblies and relative positions of the different parts, as well as the stationary and movable surfaces of a pump are aspects and parameters that must be defined when designing the pump. The final objective of the design is to get a maximum efficiency of the pump with a minimum or no side effects resulting from the energy transferred to the fluid during the impelling thereof. Particularly in the case of a blood pump design, the aim is to reach to a pump having a maximum efficiency without side effects causing blood damage and/or blood clotting during operation. Another important objective is to have a pump having a minimum size.

The side effects resulting from the energy transferred during rotation of the pump comprise the generation of secondary or side flows, vortex, cavitation and separation of the flow from the surfaces of the stationary and movable parts of the pump.

The continuous fluid flow behavior through a rotary pump provided with blades is mathematically defined by the Euler equation. According to Euler, pressure energy imparted by the rotor is proportional to the increment of the tangential component of velocity. Analysis of the Euler equation is made through the so called velocity triangles shown in FIG. 1 for a conventional scheme. Vectors represent averaged velocities on a flow surface and the letter references used in FIG. 1 are:

| | |
|---|---|
| ω | angular speed |
| R | radius |
| u = ω.R | rotation velocity |
| C | absolute velocity |
| W | relative velocity |
| $C_u$ | tangential component of absolute velocity | index 1 is used for the pump inlet
index 2 is used for the pump outlet

The Euler equation applied to a conventional rotary pump is:

$$(R \cdot C_u)_2 - (R \cdot C_u)_1 = \frac{g \cdot H}{\eta \cdot \omega}$$

where,

H Head

G Acceleration due to gravity

η Efficiency if $C_{u1} = 0$, we have $$C_{u2} = \frac{g \cdot H}{R_2 \cdot \eta \cdot \omega}$$

This is the reason why traditional pump designs include stator blades at the pump outlet, thus trying to reduce as much as possible the tangential component of the velocity and transform the kinetic energy into pressure energy.

Although many efforts have been made to eliminate or at least reduce the above mentioned side effects, by reducing or eliminating the above tangential component, for example, no solutions have been found hereinbefore. When a small Reynold's number is involved, that is when one handles small pumps and/or viscous liquids, stator blades at the pump outlet can not effectively reduce the tangential component of the velocity and transform kinetic energy into pressure energy, no matter the shape or number of blades provided. Therefore, flow separation and side flows are formed at the stator blades which cause hemolysis and blood clotting.

There are indeed several patents disclosing pumps with stator blades at the pump outlet with the purpose of eliminating, as much as possible, the tangential component of fluid speed exiting the impelling stage of the pump. U.S. Pat. No. 4,846,152, issued to Richard K. Wampler, discloses a miniature intravascular blood-pump formed as a single stage with a rotor and an elongated stator, the rotor having two rows of blades and the stator having a single row of blades, within a tubular housing. The blades of the stator are reversed-twisted and have an unusual length to straightens and slow the blood flow so as to prevent the deposit of blood particles. This stator, however, does not provide for the elimination of any tangential component of the flow speed at the exit of the pump.

U.S. Pat. No. 4,908,012 to John C. Moise, discloses an implantable ventricular assistance pump having a tube in which a pump rotor and stator are coaxially contained, and purge fluid is introduced into stator blades of the pump to avoid creation of discontinuities in the blood path wall. The object of this cited patent is to reduce the size of the implant and minimize the risk of infection by reducing vibration, minimizing the percutaneous conduit, and directing most of the heat generated by the pump into the blood. The problem of the flow kinetic energy is not addressed and, in fact, the provision of the bladed stator does not reduce the tangential component of the flow speed.

U.S. Pat. No. 5,209,650 to Guy B. Lemieux, discloses a pump integral with an electric motor and impeller assembly that rotates within a stator casing and is supported on hydrostatic radial and thrust bearings so as to avoid having to provide external seals or friction type bearings. Although rotors rotating in opposite directions are provided in this patent, it is clearly disclosed in its specification that the invention addresses the problems that occur with leaking mechanical seals and worn bearings. While Lemieux specifically includes stay vanes pitched to diffuse the liquid from the second stage integral rotor and impeller assembly, the problem of kinetic energy and tangential components of the blood flow is not considered, and it can not be overcome in any way by providing, as disclosed and illustrated in this patent, axial rotors separated by axial stators.

U.S. Pat. No. 5,211,546 to Milton S. Issacson discloses an axial flow blood pump including stator blades and rotor, the object of which is to minimize the structure by which the rotor is suspended with respect to the stator to minimize the overall diameter of the motor and pump combination. No considerations are made relating to the tangential components of the blood flow and the side effects resulting thereof.

U.S. Pat. No. 5,588,812 to Lynn P. Taylor discloses an implantable electric blood pump having a motor stator and a rotor, the stator including blades for slowing and de-spinning the blood flow.

U.S. Pat. No. 5,678,306 to Richard J. Bozeman discloses a method for optimizing each of a plurality of blood pump configuration parameters in the known pump components and variations. While Bozeman includes a diffuser with five to eight fixed blades for deaccelerating and redirecting the outflow at blood flow path exit to boost pump performance, the problem of the tangential components of the speed is not solved.

U.S. Pat. No. 5,707,218 issued to Timothy R. Maher discloses an axial-flow blood pump having a rotor suspended in ball-and-cup bearings which are blood-cooled but not actively blood-lubricated. While, Maher includes outlet stator blades for slowing and de-spinning the blood flow for discharge into the pump outlet, again, the problem of the tangential components in the blood flow is not addressed.

Other rotary pumps are known from U.S. Pat. Nos. 4,779,614; 5,040,944; 5,112,292 and 5,692,882 but these documents have not addressed the problem of the tangential component of the flow velocity.

Concluding, the problem of the flow separation and secondary flows have not been addressed and solved by any of the patents mentioned above.

It would be therefore convenient to have a continuous axial-flow pump having a minimum quantity of components and capable of providing a continuous flow without side effects resulting from the kinetic energy of the circulating fluid and affecting the fluid integrity, particularly to avoid the blood damage and blood clotting by eliminating the flow separation and secondary flows.

3. Summary of the Invention

It is therefore one object of the present invention to provide a continuous axial-flow pump for impelling a fluid under a continuous pattern without side effects to minimize and eliminate damage to fluid, the pump comprising two axial adjacent rotors rotating in opposite directions.

It is still another object of the present invention to provide a continuous axial-flow pump having at least one stage, comprising an outer casing and rotor means mounted in the casing, the rotor means comprising at least two adjacent rotors rotating in opposite directions.

It is a further object of the present invention to provide a rotary assembly for providing a continuous axial-flow, comprising at least two adjacent rotors rotating in opposite directions and capable of being mounted in a pump, preferably a blood pump.

According to the invention, it has been found that with the substitution of the stator blades at the pump outlet of a conventional pump by a rotating impeller rotating in a direction opposite to the one of the conventional rotor, the pump is effective in eliminating the tangential component of the flow velocity and transforming the kinetic energy of the flow into pressure energy.

For defined combinations of speeds and outputs, the flow at the pump outlet is axial without flow separation, and secondary flows disappear.

The above and other objects, features and advantages of this invention will be better understood when taken in connection with the accompanying drawings and description.

BRIEF DESCRIPTION OF THE DRAWINGS

The present invention is illustrated by way of example in the following drawings wherein.

DESCRIPTION OF THE PREFERRED EMBODIMENTS

Figure 1:
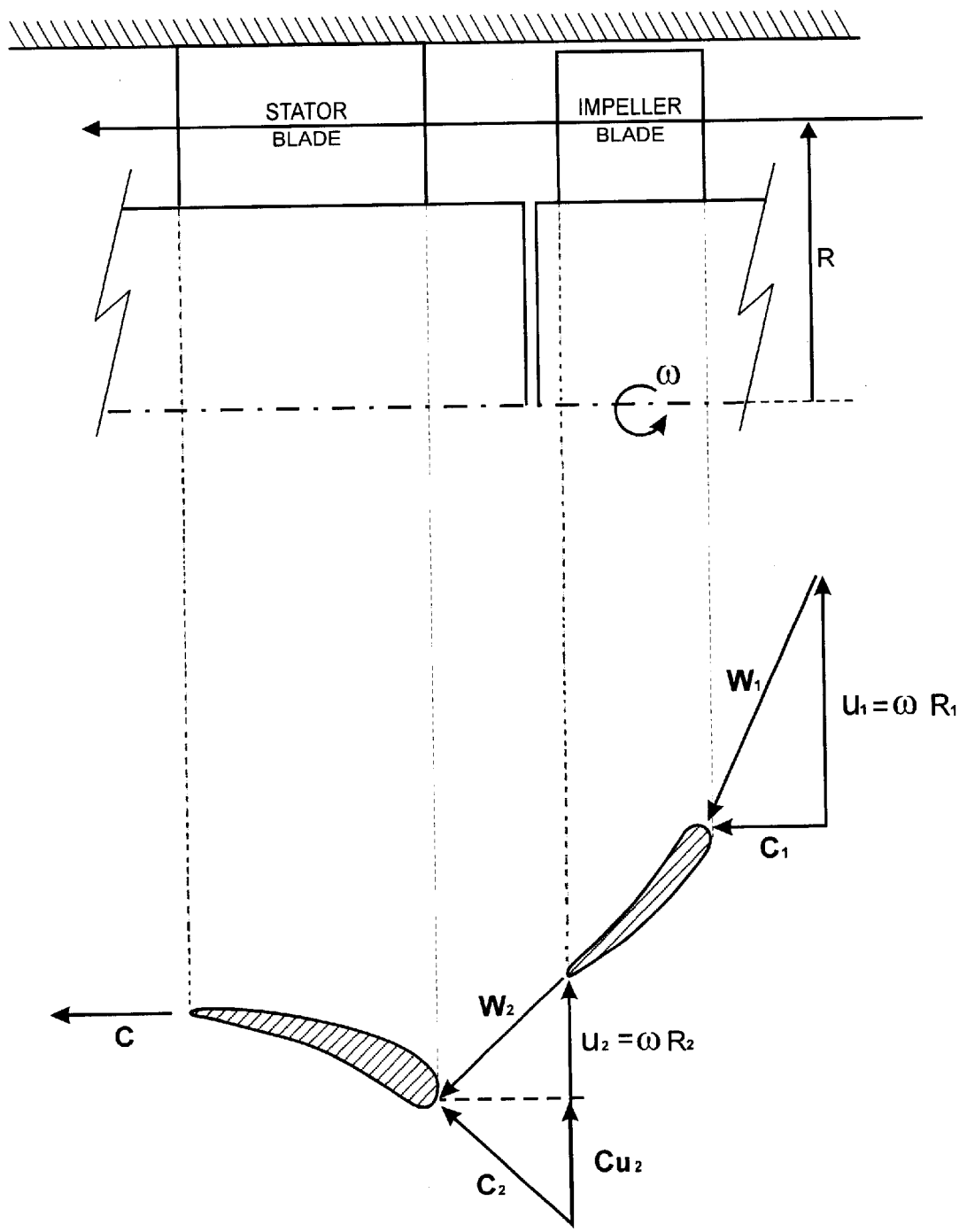
FIG. 1 shows a diagram of velocity triangles according to the Euler equation for a conventional rotary pump.
Figure 2:
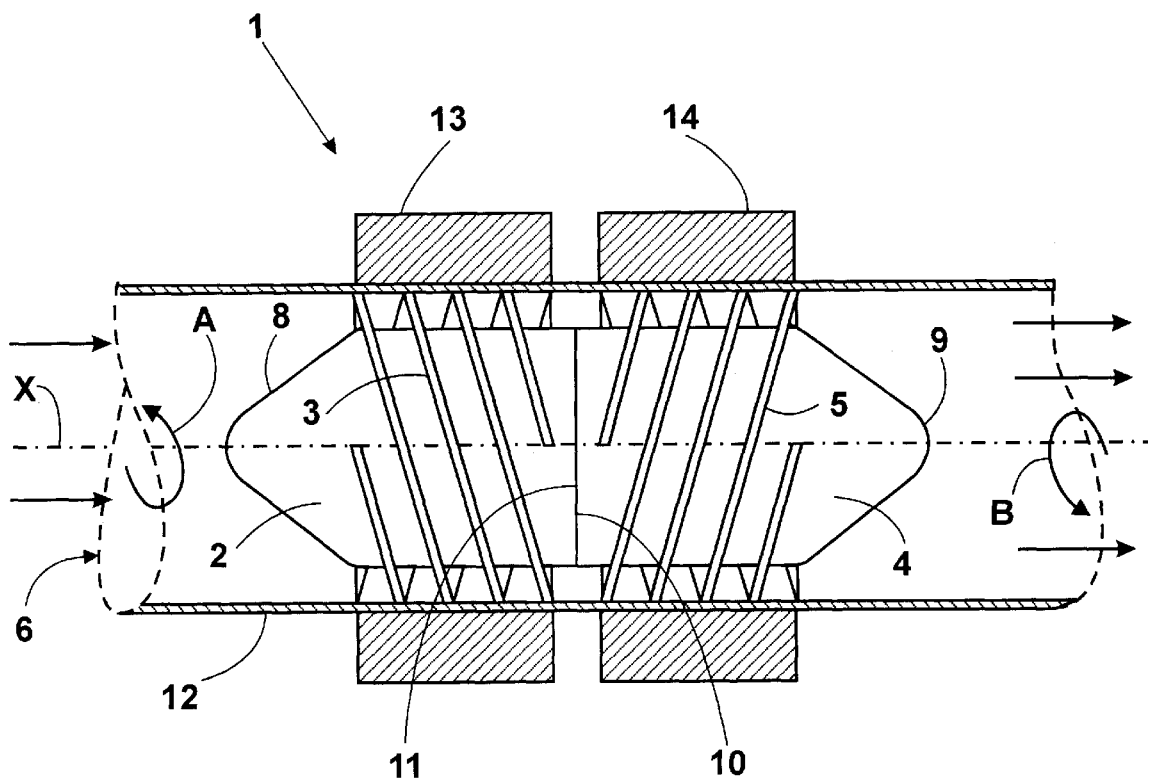
FIG. 2 shows an elevation view, partially in section, of a basic construction for a pump in accordance with the invention.

Now referring in detail to the drawings illustrating the pump of the invention it may be seen from FIG. 2 that the inventive rotary pump indicated by general numeral reference 1 is comprised of two adjacent impellers or rotary means, preferably a first rotor 2 having impeller means comprising twisted blades 3, and a second rotor 4 provided with impeller means comprising twisted blades 5. Blades 5 are twisted in opposite or reversed direction relative to blades 3. Rotors 2, 4 rotate, according to the concepts of the invention, in opposite directions, as shown by arrows A, B, around longitudinal axis X of the pump. According to the rotary directions indicated by arrows A, B, the left side of FIG. 2 corresponds to inlet 6 of the pump while the right side of the Figure corresponds to outlet 7 of the pump. Preferably, opposite outer ends 8, 9 of rotors 2, 4 are cone-shaped to accommodate the fluid flow. Inner facing ends 10, 11 of rotors 2, 4 are adjacent so that an outlet of rotor 2, when rotor 2 is an inlet rotor, is adjacent to an inlet of rotor 4 when rotor 4 defines an outlet rotor. The "inlet" and "outlet" terms are used to qualify the rotor that is at the inlet side 6 or at the outlet side 7 of the pump. Obviously, the inlet and outlet of the pump will depend on the rotary directions of the rotors. Although the directions are indicated with arrows A, B these directions can be inverted if desired.

Rotors 2, 4 may be conveniently arranged within a casing, preferably a cylindrical, tubular casing and stator motor components 13, 14 may be provided to drive the rotors. First rotor 2 rotates by the driving action of stator motor 13 and transfers energy to the fluid flow, preferably the blood flow, and increases the tangential component of velocity of the flow. Rotor 4 counter rotates under the action of stator motor component 14 and transfers pressure energy to the flow as well as eliminates the above cited tangential component at the outlet side of the pump for given combinations of heads and discharges or outputs.

Figure 3:
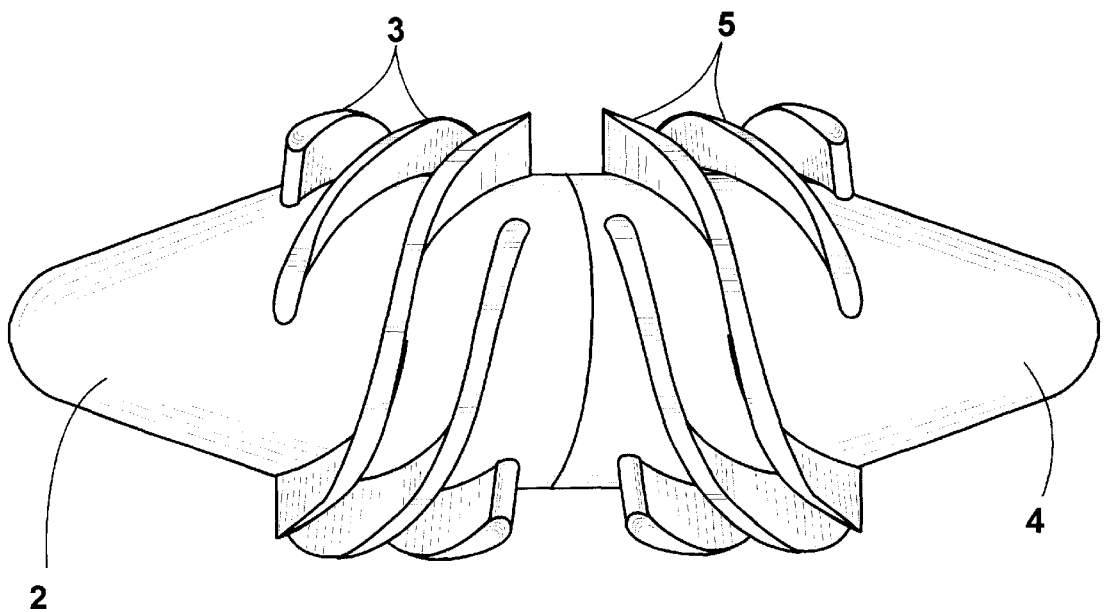
FIG. 3 shows a perspective view of two adjacent impelling rotors according to the invention.

FIG. 3 shows rotors 2, 4 in a perspective view wherein blades 3, 4 are clearly depicted to see the location and development thereof around the corresponding rotor. Blades 3, 4 are twisted around the rotors, more precisely, the blades extend hellicaly over the rotors with blades 3 defining a first-direction helix and blades 4 defining a second-direction helix opposite to the first-direction.

Figure 4:
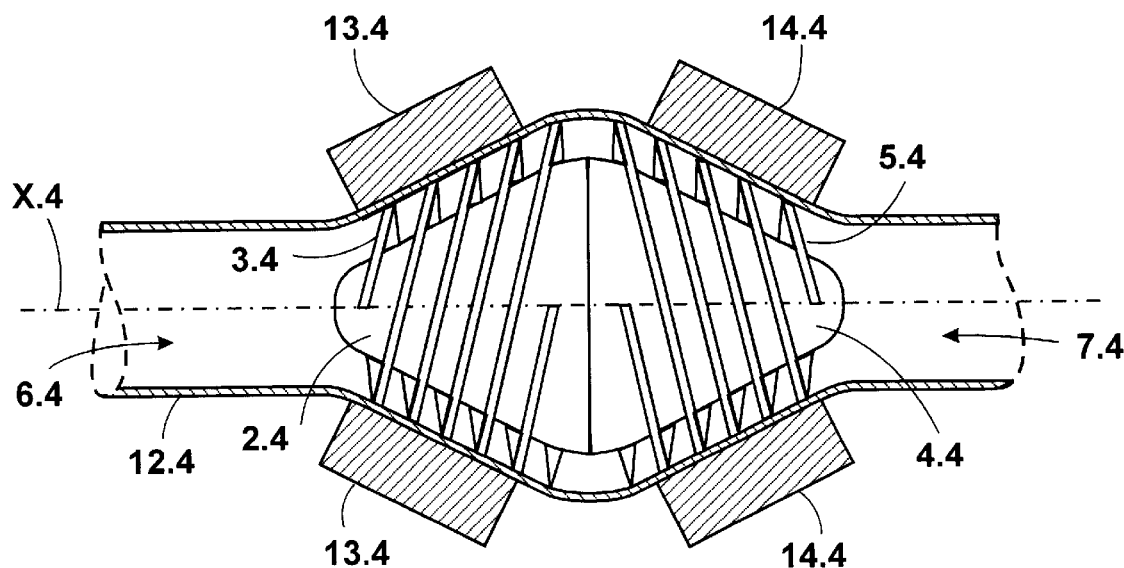
FIG. 4 shows an elevation view, partially in section, of a basic construction for a pump in accordance with another embodiment of the invention.

FIG. 4 shows another embodiment of the invention wherein each rotor has an entire cone-shape and both rotors are faced and adjacent by their cone-bases. The numeral references used for identifying the equivalent components of the several embodiments comprise the same numeral reference used in FIGS. 2, 3 plus a dot (.) and the number of the corresponding Figure. Thus, the rotors in FIG. 4 are indicated with 2.4, 4.4. Casing 12.4 has a profile to accommodate rotors 2.4, 4.4 inside and motor components 13.4, 14.4 will be arranged correspondingly around casing 12.4, as it clearly shown.

Figure 5:
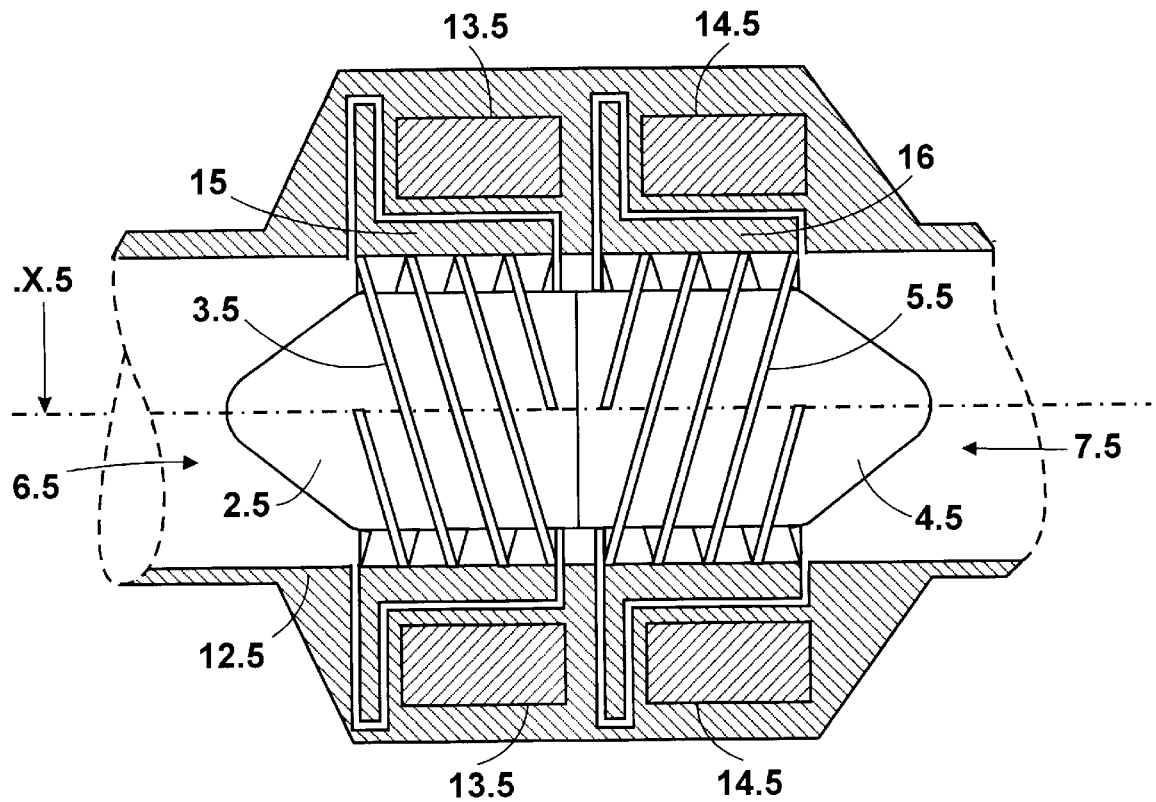
FIG. 5 shows an elevation view, partially in section, of a basic construction for a pump in accordance with even another embodiment of the invention.

FIG. 5 shows another embodiment of the invention wherein each stator motor component 13.5, 14.5 is combined with a band 15, 16 for hydrodynamic suspension of the components.

Figure 6:
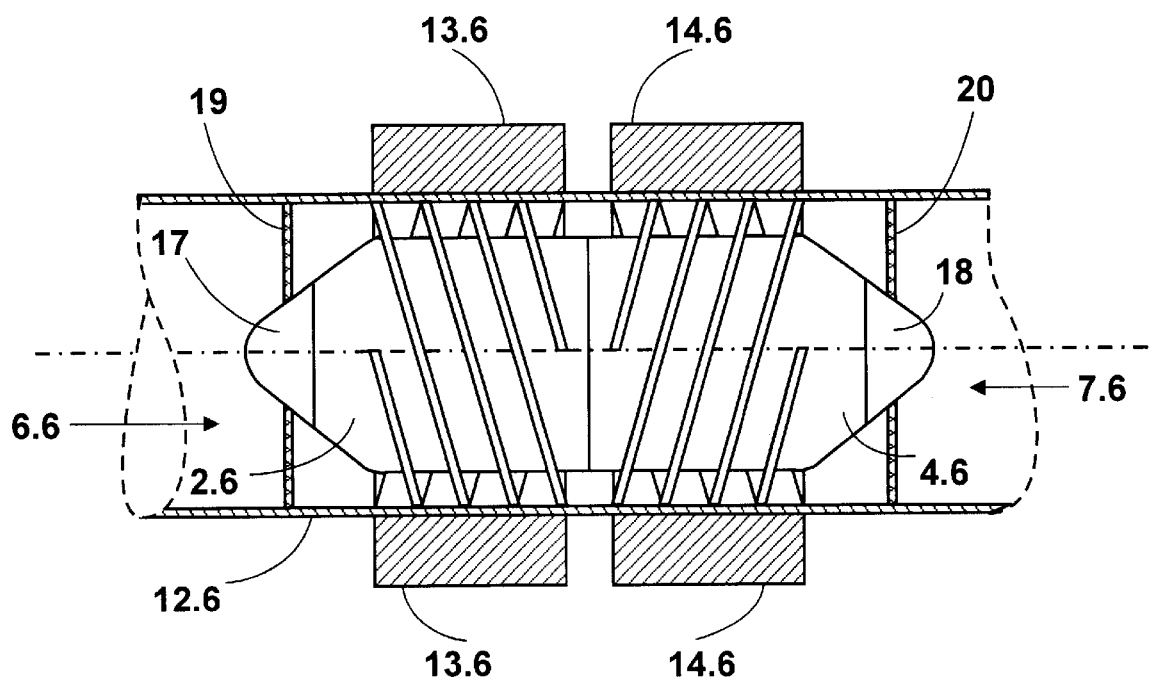
FIG. 6 shows an elevation view, partially in section, of a basic construction for a pump in accordance with a further embodiment of the invention.

Finally, FIG. 6 shows another embodiment of the invention wherein each outer end of the rotors comprises a ball-socket bearing 17, 18 that is mounted on a corresponding support 19, 20 which in turn is fixed to casing 12.6.

It is to be noted that although motor components 13, 14 have been illustrated the rotors may be actuated through other means such as one or more rotary wires connected to the rotors.

Figure 7:
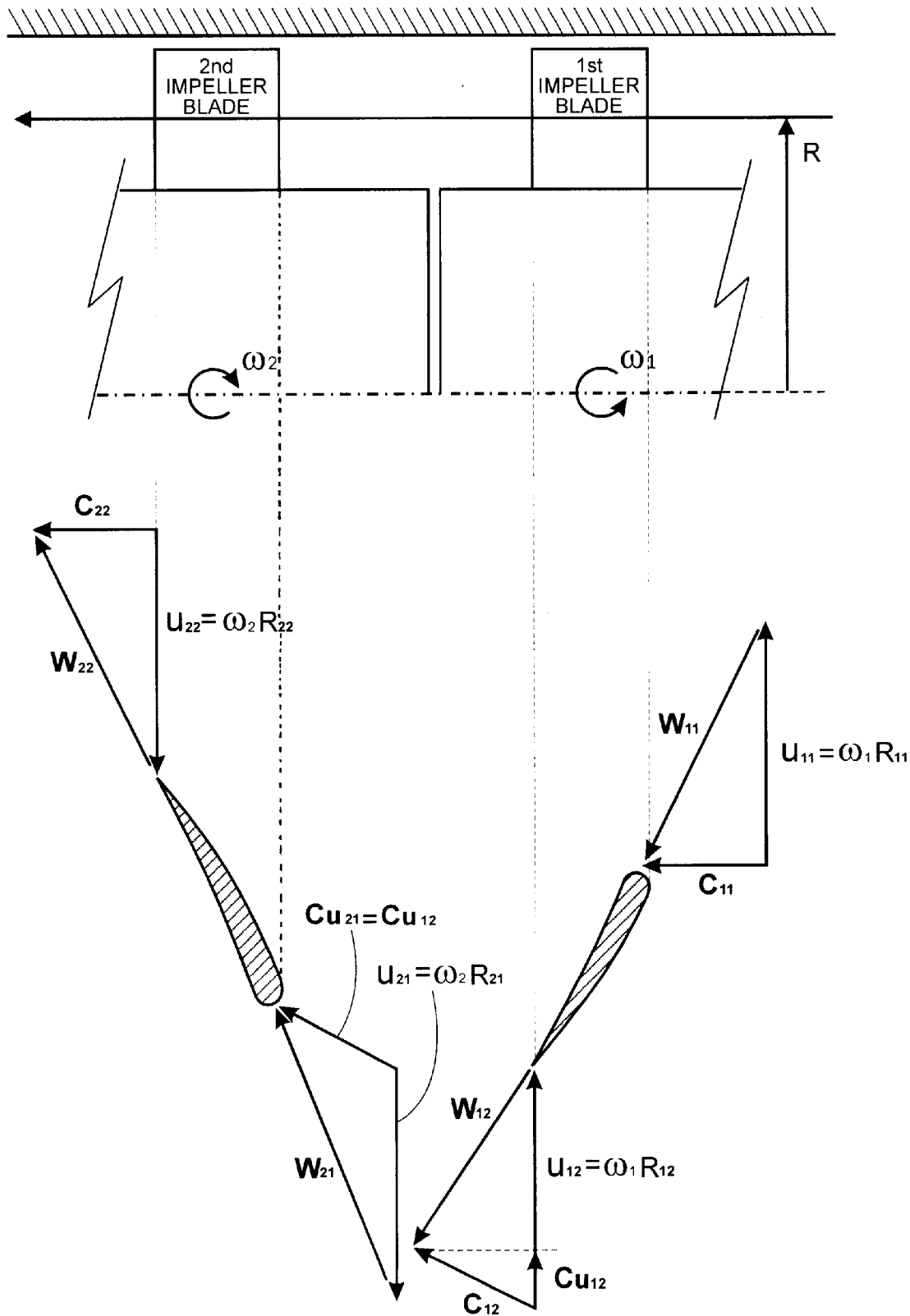
FIG. 7 shows a diagram of velocity triangles according to the Euler equation for a rotary pump according to the present invention.

Referring to FIG. 7 the average velocity triangles of Euler equation for the present invention may be seen, where:

$\omega_1$, $\eta_1$, $H_1$ are angular speed, efficiency and head of the $1^{st}$ impeller, namely the first rotor;

$\omega_2$, $\eta_2$, $H_2$ are angular speed, efficiency and head of the $2^{nd}$ impeller, namely the second rotor;

in double index the first one is the number of the impeller and the second means:

1—inlet of impeller
    2—outlet of impeller.

The Euler equation for the first impeller is $$(R \cdot C_u)_{12} - (R \cdot C_u)_{11} = \frac{g \cdot H_1}{\eta_1 \cdot \omega_1}$$

If $C_{u11}=0$, then $$(R \cdot C_u)_{12} = \frac{g \cdot H_1}{\eta_1 \cdot \omega_1} \quad \text{and}$$

$$C_{u12} = \frac{g \cdot H_1}{R_{12}\eta_1 \cdot \omega_1}$$

For the second impeller is $$(R \cdot C_u)_{22} - (R \cdot C_u)_{21} = \frac{g \cdot H_2}{\eta_2 \cdot \omega_2}$$

since $(R.C_u)_{21}=(R.C_u)_{12}$

Then $$(R \cdot C_u)_{22} = \frac{g \cdot H_2}{\eta_2 \cdot \omega_2} + \frac{g \cdot H_1}{\eta_1 \cdot \omega_1}$$

The total head is $$H = H_1 + H_2$$

Finally,

If $\quad \dfrac{g \cdot H_2}{\eta_2 \cdot \omega_2} = -\dfrac{g \cdot H_1}{\eta_1 \cdot \omega_1},$ then, $(R.C_u)_{22} = 0$ and $C_{u22}=0$ Therefore, the flow at the pump outlet is totally axial.

With ($H_1$ and $H_2$) and ($\eta_1$ and $\eta_2$) having the same sign, note that the equation $$\frac{g \cdot H_2}{\eta_2 \cdot \omega_2} = -\frac{g \cdot H_1}{\eta_1 \cdot \omega_1}$$

is feasible only if $\omega_1$ and $\omega_2$ have opposite signs. This is the reason why our proposed scheme includes two impellers rotating in opposite directions.

Stator blades at the pump outlet are not necessary any more. There is an increase of hydraulic efficiency and there is a dramatic reduction of blood damage and blood clotting.

The present invention provides a continuous flow rotary pump housing defining a blood flow path therethrough, and two impellers (rotors) with blades mounted within the pump housing. Rotors are adjacent and counter rotate to each other, While preferred embodiments of the present invention have been illustrated and described, it will be obvious to those skilled in the art that various changes and modifications may be made therein without departing from the scope of the invention as defined in the appended claims.

We claim:

1. A continuous axial flow blood pump having at least one stage, comprising an outer casing and rotor assembly mounted in the casing, the rotor assembly comprising:

at least two adjacent rotors rotating in opposite directions with angular speeds $\omega_1$ and $\omega_2$ complying with the formula:

$$\frac{g \cdot H_2}{\eta_2 \cdot \omega_2} = -\frac{g \cdot H_1}{\eta_1 \cdot \omega_1}.$$

2. A method of pumping blood comprising the steps of:

providing intake and exhaust conduits;

providing blood; and pumping the blood between the intake and exhaust conduits using a continuous axial-flow pump having at least one stage comprising an outer casing and rotor assembly mounted in the case, the rotor assembly comprising at least two rotors rotating in opposite directions, the rotors being independently driven.

3. A method of pumping blood comprising the steps of:

providing intake and exhaust conduits;

providing blood; and pumping the blood between the intake and exhaust conduits using a continuous axial-flow pump having at least one stage comprising an outer casing and rotor assembly mounted in the casing, the rotor assembly comprising at least two rotors rotating in opposite directions and in compliance with the following formula:

$$\frac{g \cdot H_2}{\eta_2 \cdot \omega_2} = -\frac{g \cdot H_1}{\eta_1 \cdot \omega_1}.$$

\* \* \* \* \*